United States Patent
Beacom et al.

(10) Patent No.: US 10,655,151 B2
(45) Date of Patent: *May 19, 2020

(54) PROCESS FOR FERMENTING SUGARS CONTAINING OLIGOMERIC SACCHARIDES

(71) Applicant: Cargill, Incorporated, Wayzata, MN (US)

(72) Inventors: Daniel R. Beacom, Wayne, PA (US); Jeffrey J. Kolstad, Wayzata, MN (US); David H. Reeder, Chanhassen, MN (US); Brian J. Rush, Minneapolis, MN (US)

(73) Assignee: Cargill, Incorporated, Wayzata, MN (US)

( * ) Notice: Subject to any disclaimer, the term of this patent is extended or adjusted under 35 U.S.C. 154(b) by 107 days.

This patent is subject to a terminal disclaimer.

(21) Appl. No.: 15/005,577

(22) Filed: Jan. 25, 2016

(65) Prior Publication Data

US 2016/0138060 A1 May 19, 2016

Related U.S. Application Data

(63) Continuation of application No. 11/547,211, filed as application No. PCT/US2005/008818 on Mar. 16, 2005, now Pat. No. 9,328,364.

(60) Provisional application No. 60/558,266, filed on Mar. 31, 2004.

(51) Int. Cl.
| | | |
|---|---|---|
| C12P 7/56 | (2006.01) | |
| C12P 19/02 | (2006.01) | |
| C12P 19/04 | (2006.01) | |
| C12P 19/16 | (2006.01) | |
| C12P 19/20 | (2006.01) | |

(52) U.S. Cl.
CPC ............... *C12P 7/56* (2013.01); *C12P 19/02* (2013.01); *C12P 19/04* (2013.01); *C12P 19/16* (2013.01); *C12P 19/20* (2013.01)

(58) Field of Classification Search
None
See application file for complete search history.

(56) References Cited

U.S. PATENT DOCUMENTS

| | | | |
|---|---|---|---|
| 4,113,509 A | 9/1978 | Leach | |
| 4,734,364 A | 3/1988 | Line | |
| 4,935,348 A | 6/1990 | Oosterhuis | |
| 5,231,017 A | 7/1993 | Lantero | |
| 5,464,760 A * | 11/1995 | Tsai | C12P 7/56 |
| | | | 127/42 |
| 5,780,275 A * | 7/1998 | Oda | C12P 7/02 |
| | | | 435/135 |
| 9,328,364 B2 * | 5/2016 | Beacom | C12P 7/56 |
| 2003/0180900 A1 | 9/2003 | Lantero | |
| 2004/0115779 A1 | 6/2004 | Olsen | |
| 2005/0233423 A1 | 10/2005 | Berka | |

FOREIGN PATENT DOCUMENTS

| | | |
|---|---|---|
| WO | 2003/095659 A | 11/2003 |
| WO | 2004/087889 A | 10/2004 |

OTHER PUBLICATIONS

Cadmus et al. "Enzymatic production of glucose syrup from grains and its use in fermentations". Cereal Chem., 1966, vol. 43, No. 6, pp. 658-669.*
Tsai et al., "An Integrated Bioconversion Process . . . ", Appl. Biochemistry and Biotechnology. vol. 70-72, p. 417 ff (1998).
Huang et al., "Ethanol Production in Simultaneous Saccharification . . . ", J. Ferment. Technol. vol. 66, 509-516 (1988).
Montesinos et al., "Role of the maltose . . . ", Bioprocess Engineering 23 (2000), 319-322.
Boles et al., "The molecular genetics of hexose transport in yeast", FEMS Microbiology Reviews 21 (1997) 85-111.
Teste et al., "Characterization of a New Multigene Family . . . ", J. Biological Chemistry vol. 285, pp. 2685-26824 (2010).
Badotti et al., "Switching the mode of sucrose utilization . . . ", Microbial Cell Factories 2008, 7:4.
Han et al., Characterization of AGT1 . . . :, Molecular Microbiology (1995), 1093-1107.
Smit et al., "The Thr505 and Ser557 residues . . . ", J. Appl. Microbiology 104 (2008) 1103-1111.

* cited by examiner

*Primary Examiner* — Vera Afremova

(57) ABSTRACT

Sugar mixtures containing nonfermentable oligomers are fermented in the presence of certain enzymes that depolymerise the oligomers simultaneously with the fermentation process.

10 Claims, No Drawings

PROCESS FOR FERMENTING SUGARS CONTAINING OLIGOMERIC SACCHARIDES

This invention relates to a process for fermenting monosaccharides that contain quantities of polysaccharide materials.

Fermentation processes are used commercially at large scale to produce organic molecules such as ethanol, citric acid and lactic acid. In those processes, a carbohydrate is fed to a microorganism that is capable of metabolizing it to the desired fermentation product. The carbohydrate and microorganism are selected together so that the microorganism is capable of efficiently digesting the carbohydrate to form the product that is desired in good yield. It is becoming more common to use genetically engineered microorganisms in these processes, in order to optimize yields and process variables, or to enable particular carbohydrates to be metabolized.

Starch is a widely available and inexpensive carbohydrate source. It is available from a wide variety of plant sources such as corn, wheat, rice, barley, and the like. Many microorganisms are not capable of metabolizing starch directly, or else metabolize it slowly and inefficiently. Accordingly, it is common to treat starch before feeding it into the fermentation process, in order to break it down into monosaccharides that the microorganism can ferment easily.

Usually, starch is hydrolyzed to form a mixture containing mainly glucose (i.e., dextrose). However, complete hydrolysis to glucose adds significant cost, so most commercially available glucose products tend to contain a small amount of fructose and various oligomeric polysaccharides. Unfortunately, many microorganisms cannot metabolize the oligomers, either, and so these carbohydrate values are wasted. Moreover, the presence of these oligomers complicates the recovery of the desired fermentation product from the fermentation medium.

So-called simultaneous saccharification and fermentation (SSF) processes are known, in which an unhydrolyzed starch is fed into a fermentation process together with enzymes that catalyse the breakdown of the starch until monosaccharides. Monosaccharides are produced and are simultaneously fermented to the desired product. SSF processes suffer from several disadvantages. The starch that is fed into SSF processes is typically not sterile. The same is true for the enzymes. Thus, sterilization must be performed in the fermentation vessel. This tends to be energy-intensive and inefficient. Further, as glucose is produced, it tends to deactivate the enzymes and slow the overall production rates.

Accordingly, an improved process by which monosaccharide feedstocks that contain quantities of oligomeric sugars can be fermented efficiently would be desirable.

In one aspect, this invention is a fermentation process subjecting a fermentation broth containing 30 g/L or less of a monosaccharide and from about 1 to about 10 g/L of one or more nonfermentable oligomeric saccharides to fermentation conditions in the presence of (A) a microorganism that ferments the monosaccharide but does not ferment at said nonfermentable oligomeric saccharides and (B) an effective amount of at least one active enzyme that depolymerizes at least one of said nonfermentable oligomeric saccharides to form a monosaccharide that is fermentable by the microorganism, under conditions such that the depolymerization of the nonfermentable oligomeric saccharide and the fermentation of the monosaccharides occur simultaneously.

In a second aspect, this invention is a process for fermenting a fermentation substrate in the presence of a microorganism, comprising
 (A) forming a starting fermentation broth containing (1) a fermentation substrate, of which (a) from about 75 to about 98% by weight is a monosaccharide that is fermentable by the microorganism to a desired fermentation product, and (b) from about 2 to about 25% by weight is one or more oligomeric saccharides that are not fermentable by the microorganism to the desired fermentation product, wherein the starting fermentation broth contains at least 30 g/L of the monosaccharide;
 (B) fermenting the starting fermentation broth in the presence of the microorganism to conditions sufficient to ferment the monosaccharide and reduce the monosaccharide concentration in the fermentation broth to less than about 30 g/L;
 (C) then adding to the fermentation broth active an effective quantity of at least one enzyme that depolymerizes at least one oligomeric saccharide in the fermentation broth to form a monosaccharide that is fermentable by the microorganism to form a desired fermentation product;
 (D) and then subjecting the fermentation broth to conditions sufficient to simultaneously depolymerize at least one oligomeric saccharide and ferment monosaccharides to form the desired fermentation product.

In a third aspect, this invention is a fermentation process comprising fermenting a fermentation broth containing up to 30 g/L of glucose and from about 1 to about 10 g/L of nonfermentable glucose oligomers in the presence of (A) a microorganism that ferments the glucose but does not ferment at said nonfermentable glucose oligomers and (B) an effective amount of at least one active enzyme that depolymerizes at least one of said nonfermentable glucose oligomers to form a monosaccharide that is fermentable by the microorganism, under conditions such that the depolymerization of the nonfermentable glucose oligomers proceed simultaneously fermentation of the glucose and the monosaccharide.

It has been surprisingly found that enzymatic depolymerization of oligomeric saccharides can occur at good rates in the presence of significant concentrations of monosaccharides. This allows for simultaneous fermentation and depolymerization of oligomers, without significant inactivation of the enzymes or reformation of 1→6 oligomers. This process provides an efficient ferment fermentation method in which relatively inexpensive carbohydrate feedstocks can be used and very high yields to the desired fermentation product are obtained at commercially reasonable rates.

The "fermentable monosaccharide" is a sugar that can be fermented by the microorganism that is used in the process, to form a desired fermentation product. The fermentable monosaccharide is preferably a pentose or hexose sugar. A particularly preferred hexose sugar is glucose.

The "nonfermentable oligomeric saccharide" is a carbohydrate oligomer in which two or more monosaccharide units are linked together via ether linkages. The oligomeric saccharide is "nonfermentable", meaning that it cannot be fermented by the microorganism to the desired fermentation product, or else that the rate of its fermentation is at not more than about 5% of the rate at which the microorganism ferments the fermentable monosaccharide under the conditions of used in the process. The degree of polymerization is preferably from about 2 to about 10, especially from about 2 to about 5, most preferably from about 2 to about 3. In the case where of oligomeric hexose sugars, those having either 1→4 or 4→6 ether linkages are suitable, although those having 1→4 ether linkages are preferred. Especially preferred nonfermentable oligomeric saccharides include oligomers of glucose such as maltose, maltotriose and isomaltotriose (all having 1→4 ether linkages), ismaltose (having a 1→6 linkage), and panose (having both 1→4 and 1→6 linkages).

Commercially available starch hydrolyzate contain about 80-98 weight % (based on carbohydrates), especially about 90-96 wt % of glucose (a fermentable monosaccharide) and from about 1-20% (based on carbohydrates, especially about 1-9% glucose oligomers which tend to be nonfermentable. These hydrolyzates may also contain small quantities (up to about 2% by weight, based on carbohydrates) of fructose and other carbohydrates. Such starch hydrolyzates are a particularly preferred fermentation substrate for use in this invention.

In this invention, simultaneous fermentation and enzymatic oligomer depolymerization occurs. In the process, active enzymes are added to a fermentation broth that up to about 30 g/L of the fermentable monosaccharide. Higher concentrations of monosaccharide tend to reduce the efficiency of the enzymatic depolymerization reaction, and are therefore undesirable. In addition, some of the enzymes will catalyze the formation of 16 polysaccharide oligomers in the presence of high concentrations of monosaccharides. The monosaccharide concentration is preferably up to about 26 and more preferably up to about 20 g/L thereof.

The broth contains up to about 10 g/L of the nonfermentable oligomeric saccharide, preferably from about 1 to about 8 g/L and more preferably about 3-6 g/L thereof. The fermentation broth is then subjected to conditions under which the fermentable monosaccharide is fermented at the same time at least one of the nonfermentable oligomeric saccharides is depolymerized. Monosaccharides that are produced in the depolymerization reaction (which may be the same or different from the starting fermentable monosaccharide) are fermented as well. The simultaneous enzymatic depolymerization and fermentation provides excellent yields and good fermentation rates.

It is usually more economical to begin a fermentation with a much higher concentration of fermentable monosaccharide. A preferred embodiment of the invention, therefore, is a process in which a starting fermentation broth containing above 30 g/L (preferably at least 40 g/L, more preferably at least 50 g/L, especially at least 55 g/L) of monosaccharide is fermented until the monosaccharide concentration is reduced to below 30 g/L, preferably below 26 g/L and more preferably below 5 g/L. The enzyme(s) is then added and simultaneous fermentation and oligomer fermentation is performed. This embodiment of the invention allows one to take advantage of the better economics that come with using higher starting concentrations of starting materials.

Any enzyme that is capable of depolymerizing the nonfermentable oligomer(s) can be used herein. The specific type of enzyme that is used is selected in relation to the particular oligomeric saccharides that are present in the fermentation broth. Enzymes of particular interest attack a 1→4 ether linkage or a 1→6 ether linkage (or both) of an oligomeric saccharide. A preferred enzyme for depolymerizing oligomers with 1→4 linkages is α-glucosidase (glucoamylase). A preferred enzyme for depolymerizing oligomers with 1→6 linkages is trans-glucosidase. Mixtures of α-glucosidase and trans-glucosidase are preferred when oligomeric saccharides of each type are present. These enzymes are commercially available from, e.g., Enzyme Biosystems (G-ZYME 99 SP (an α-glucosidase product) and Genencor (Transglucosidase L-500). In some instances, commercial grades of α-glucosidase are not highly refined, and contain various quantities of other enzymes that attack the 1→4 and/or 1→6 linkage of oligomeric saccharides. These "crude" grades of α-glucosidase are among the preferred types of enzymes. An example of such a "crude" grade is GC702, from Genencor.

The amount of enzyme that is used will depend somewhat on the particular enzyme, the desired rate of reaction, and the particular oligomeric polysaccharide(s) that are present. Typically, the enzyme is used in a quantity sufficient to provide about 5-10,000 μL of enzyme/L of fermentation broth. A more preferred quantity is from about 10-1000 μL/L and an even more preferred quantity is from about 25-500 μL/L.

Examples of chemicals that are produced in commercial fermentation products are ethanol, lactic acid, citric acid, malonic acid, hydroxy butyric acid, and acetic acid.

The microorganism is one which can ferment the fermentable monosaccharide to the desired fermentation product. As such, the particular microorganism used is selected in relation to the fermentation substrate, as well as the fermentation product that is desired. The microorganism may be naturally occurring, or may be a mutant or recombinant strain. Examples of microorganisms include various species of bacilli, lactobacilli and yeast, including wild-types and mutated or recombinant types.

Suitable microorganisms useful for producing lactic acid include wild-type bacteria from the genera *Lactobacillus, Pediococcus, Lactococcus* and *Streptococcus* and wild-type fungi of the genera *Rhizopus*. In addition, recombinant yeast strains of the genera *Kluyveromyces, Pichia, Hansenula, Candida, Trichosporon,* or *Yamadazyma*, having exogenous LDH genes are suitable. Such recombinant yeast strains are described in WO 99/14335, WO 00/71738 and WO 02/42471, for example.

The fermentation broth will also include water and preferably includes nutrients, such as proteins (or other nitrogen source), vitamins and salts, which are necessary or desirable for cell function. Other components may also be present in the fermentation broth, such as buffering agents, fermentation products (which tend to accumulate as the fermentation progresses), and other metabolizes. In cases where the fermentation is an acid, it is common to buffer the broth with a base such as calcium hydroxide or calcium carbonate, in order to maintain a pH at which the microorganism functions well.

Conditions are selected so that fermentation and enzymatic depolymerization of the oligomers occur simultaneously. Although conditions can vary depending on the particular microorganism, enzyme and desired fermentation product, typical conditions include a temperature of from about 20° C., preferably from about 30° C. to about 50° C., more preferably about 45° C. Usually the reaction mixture is agitated. The process can be run batch-wise, semi-continuously, or continuously.

The process is preferably continued until as much of the fermentation substrate is converted to the desired fermentation product as is economically feasible. It is recognized, however, that in many instances it will not be cost-effective to attempt to ferment 100% of the substrate. It is preferred to conduct the process so that at least 50%, more preferably at least 60%, especially at least 75%, of the nonfermentable oligomers are converted to fermentable monosaccharides and fermented to the desired product. Final concentrations of nonfermentable oligomers are preferably below about 3 g/L, more preferably below about 2 g/L, and especially below about 1 g/L. Final concentrations of fermentable monosaccharides are preferably below 1 g/L, especially below 0.1 g/L.

The fermentation product is recovered from the fermentation broth. The manner of accomplishing this will depend on the particular product. However, in general, the microorganism is separated from the liquid phase, typically via a filtration step, and the product recovered via, for example, distillation, extraction, crystallization, membrane separation, osmosis, reverse osmosis, or other suitable technique.

Approximately 4000 L of an aqueous fermentation broth containing enough of a 95% glucose syrup to provide 153 g glucose/kg of broth is prepared. The 95% dextrose syrup contains various oligomeric species as set forth in Table 1 below. The fermentation broth includes a nutrient package to promote microorganism growth and activity.

The broth is fermented to produce lactic acid at 45° C. using a bacterium at a concentration of about 4 g cells/L. Lime is added as needed to maintain the broth pH at about 6.2. Lactic acid (in the form of the calcium salt) is produced at the rate of about 1.6 g/kg/hr. The fermentation is continued until the glucose concentration in the broth is reduced to under 7 g/L. 400 µL/L of α-glucosidase and 25 µL/L of trans-glucosidase are added. A sample of the broth is taken and analysed for glucose, maltose, isomaltose, maltotriose, panose and isomaltotriose, with the following results:

TABLE 1

| Saccharide | Concentration (g/L) |
|---|---|
| Glucose | 6.730 |
| Maltose | 3.158 |
| Isomaltose | 1.390 |
| Maltotriose | 0.033 |
| Panose | 0.768 |
| Isomaltotriose | 0.062 |
| Total oligomers | 5.932 |

At the time of enzyme addition, lactic acid concentration is 121 g/kg. After the enzyme addition, the fermentation is continued under the same conditions as before. A sample of the broth is taken at several intervals and analyzed for saccharides as before. Results are as follows:

TABLE 2

| Saccharide | Time | | | |
|---|---|---|---|---|
| | 4 h | 9 h | 25.5 h | 63 h |
| Glucose | 1.110 | 0.090 | 0.058 | ~0 |
| Maltose | 0.000 | 0.000 | 0.000 | 0.000 |
| Isomaltose | 1.267 | 1.152 | 0.353 | 0.000 |
| Maltotriose | 0.000 | 0.040 | 0.000 | 0.000 |
| Panose | 0.396 | 0.376 | 0.028 | 0.042 |
| Isomaltotriose | 0.100 | 0.092 | 0.037 | 0.050 |
| Total Oligomers | 1.762 | 1.660 | 0.418 | 0.092 |

The data in Table 2 show that all five of the tracked oligomeric saccharides were substantially depolymerised after the enzyme addition. Simultaneous fermentation is indicated by the glucose levels, which continued to drop throughout the process even though additional glucose was being generated as the oligomers were depolymerised. Overall substrate concentrations are reduced in this example from 153 g/L to less than 0.1 g/L. Final lactic concentration is 126 g/kg of broth.

Another fermentation is performed on a smaller scale, using about 1.9 L of a fermentation broth similar to that described in Table 1, except that starting glucose concentration is about 125 g/L. Fermentation is conducted for about 35 hours under the conditions described in Example 1, at which time the glucose concentration is reduced to 26 g/L. A sample is taken at this point and analyzed for saccharides. 400 µL/L of α-glucosidase is then added and the fermentation continued under the same conditions. Samples are taken at 3, 8 and 27 hours after enzyme addition, with results as shown in Table 3.

TABLE 3

| Saccharide | Time | | | |
|---|---|---|---|---|
| | At time of enzyme addition | 3 h | 8 h | 27 h |
| Glucose | 26.00 | 18.90 | 10.20 | 0.091 |
| Maltose | 2.905 | 0.545 | 0.496 | 0.309 |
| Isomaltose | 1.420 | 1.361 | 1.292 | 1.095 |
| Maltotriose | 0.188 | 0.000 | 0.000 | 0.000 |
| Panose | 0.505 | 0.217 | 0.105 | 0.131 |
| Isomaltotriose | 0.159 | 0.111 | 0.066 | 0.068 |
| Total Oligomers | 4.367 | 2.234 | 1.959 | 1.603 |

The data in Table 3 again shows that fermentation and enzymatic depolymerization of polysaccharides proceed simultaneously under these conditions. In this example, the oligomers having 1→4 ether linkages are converted in good yield to monosaccharides. Isomaltose is not significantly depolymerised in this example because the α-glucosidase does not efficiently promote the hydrolysis of the 1→6 ether linkage that exists in isomaltose.

The invention claimed is:

1. A process for fermenting a fermentation substrate in the presence of a microorganism, comprising
    (A) forming a starting fermentation broth containing a starch hydrolysate containing 80-98 weight % (based on carbohydrates) of glucose and 1-20 weight % (based on carbohydrates) of glucose oligomers that are not fermentable by the microorganism, wherein the starting fermentation broth contains at least 30 g/L of glucose;
    (B) fermenting the starting fermentation broth in the presence of the microorganism to conditions sufficient to ferment the glucose and reduce the glucose concentration in the fermentation broth to less than 30 g/L;
    (C) then adding to the fermentation broth an effective quantity of a least one enzyme that depolymerizes at least one glucose oligomer in the fermentation broth to form glucose;
    (D) and then subjecting the fermentation broth to conditions sufficient to simultaneously depolymerize the glucose oligomers and ferment the glucose.

2. The process of claim 1 wherein the starting fermentation broth contains at least 40 g/L of glucose.

3. The process of claim 1 wherein the starting fermentation broth contains at least 50 g/L of glucose.

4. The process of claim 1 wherein the starting fermentation broth contains at least 55 g/L of glucose.

5. The process of claim 1 wherein the fermentation broth at the start of step (C) contains up to 10 g/L of glucose oligomers that are not fermentable by the microorganism.

6. The process of claim 4 wherein the fermentation broth at the start of step (C) contains up to 10 g/L of glucose oligomers that are not fermentable by the microorganism.

7. The process of claim 1 wherein the fermentation broth at the start of step (C) contains up to 8 g/L of glucose oligomers that are not fermentable by the microorganism.

8. The process of claim 4 wherein the fermentation broth at the start of step (C) contains up to 8 g/L of glucose oligomers that are not fermentable by the microorganism.

9. The process of claim 1 wherein the at least one enzyme includes trans-glucosidase or a mixture of α-glucosidase and trans-glucosidase.

10. A process for fermenting a fermentation substrate in the presence of a microorganism, comprising
  (A) forming a starting fermentation broth containing a starch hydrolysate containing 80-98 weight % (based on carbohydrates) of glucose and 1-20 weight % (based on carbohydrates) of glucose oligomers that are not fermentable by the microorganism, wherein the starting fermentation broth contains at least 30 g/L of glucose;
  (B) fermenting the starting fermentation broth in the presence of the microorganism to conditions sufficient to ferment the glucose and reduce the glucose concentration in the fermentation broth to less than 30 g/L;
  (C) then adding to the fermentation broth an effective quantity of a least one enzyme that depolymerizes at least one glucose oligomer in the fermentation broth to form glucose;
  (D) and then subjecting the fermentation broth to conditions sufficient to simultaneously depolymerize the glucose oligomers and ferment the glucose to form a fermentation product selected from the group consisting of ethanol, lactic acid, citric acid, malonic acid, hydroxy butyric acid, and acetic acid.

* * * * *